Figure 1:
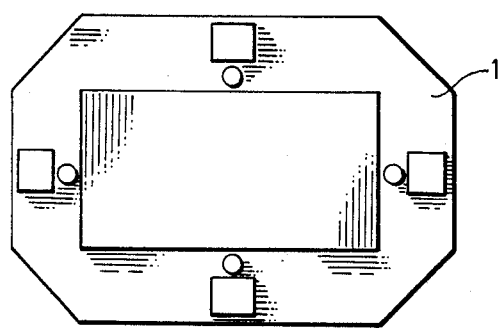

United States Patent [19]

Ober et al.

[11] Patent Number: 4,958,925
[45] Date of Patent: Sep. 25, 1990

[54] EYE MOVEMENT MEASUREMENT DEVICE WITH MULTIPLE LIGHT EMITTING AND DETECTING ELEMENTS

[75] Inventors: Jan K. Ober, Poznan, Poland; Per Udden, Hofstrasse 1, Ch-6064 Kerns, Switzerland

[73] Assignee: Per Udden, Kerns, Switzerland

[21] Appl. No.: 244,160

[22] Filed: Sep. 14, 1988

[30] Foreign Application Priority Data

Sep. 21, 1987 [SE] Sweden ............................ 8703639

[51] Int. Cl.$^5$ ............................................. A61B 3/14
[52] U.S. Cl. ................................................... 351/210
[58] Field of Search ............................. 351/209, 210; 128/303.1

[56] References Cited

U.S. PATENT DOCUMENTS 4,102,564  7/1978  Michael.

Primary Examiner—Rodney B. Bovernick
Attorney, Agent, or Firm—Oblon, Spivak, McClelland, Maier & Neustadt

[57] ABSTRACT

In a device for measuring the movements of a person's eye there are one or more sets of cooperating light detecting elements and light emitting elements intended primarily for measuring in chosen selected directions. Each set could consist of two light detecting elements located at a distance on each side of the eye and symmetrically with respect to the eye and in a symmetry plane of the eye containing the direction chosen. The associated light emitting elements are located, also symmetrically, in a plane substantially orthogonal to the plane with the light detecting elements. When many sets of cooperating light emitting and detecting elements of this kind are combined into a symmetrical or semisymmetrical arrangement, this permits selecting, for an eye movement in a given direction, the most suitable set for detecting the eye movement in this direction. Only one set of light emitting elements, assigned to the axis of measurement, is active at a time. For measuring the eye movement along two or more axes the related emitting elements are activated alternately in a repetitive sequence.

8 Claims, 1 Drawing Sheet

EYE MOVEMENT MEASUREMENT DEVICE WITH MULTIPLE LIGHT EMITTING AND DETECTING ELEMENTS

This invention relates to a device for measuring the movements of a person's eye, comprising light emitting and detecting elements located at a distance from the eye.

In prior art devices as e.g. described in the published International Application WO No. 86/03113, the movements of an eye are measured by measuring the light, emitted by a light emitting element and reflected by the eye, by means of a light detecting element. These light detecting elements and light emitting elements are placed on a common supporting frame located at a distance from the eye. In these kind of devices, generally, the eye movements in a special direction are measured, but obviously more light detecting and emitting elements could be arranged on the frame to permit measurement of the eye movements in more directions. However, when the eye moves in a direction, which is appropriate for measuring by means of a special set of light emitting elements and detecting elements, also, the other light emitting and detecting elements are influenced. It will require a complex calibration to separate these influences from each other.

To minimize this interference or "cross-talk" between different sets of light detecting elements and emitting elements, the invention proposes a new way of arranging and connecting these light emitting elements and detecting elements. The characteristics of this arrangement are given in the accompanying claims.

Thus, to measure the movements of the eye in a special direction, a set of cooperating light emitting and detecting elements is provided. This set generally has the light detecting elements located in parallel to said direction and the light emitting elements, which provide light pulses to be detected by these associated detecting elements, are arranged in a direction substantially or approximately perpendicular to the direction of the light detecting elements. One or preferably two or more such sets are provided according to the invention.

In a suitable embodiment for measuring the eye movement in one direction, every set of associated light emitting elements and light detecting elements comprises two light emitting elements and two light detecting elements, arranged symmetrically in respect of the eye. This means that this set has a mirrorlike symmetry with respect both to the planes passing through the light emitting elements and the light detecting elements.

When two sets of operating light emitting and detecting elements are provided, these are preferably arranged orthogonally to each other or near this position. In this way the different eye movements can easily be separated from each other.

The light emitting elements and detecting elements are also preferably located on a common supporting frame, which is also provided with the necessary connections between these elements, possibly some electronic assisting circuits and connecting elements for connection to a remotely placed electronic unit. This supporting frame has an aperture, suitably arranged in the center thereof. When the device comprises several sets of independent light emitting and detecting elements, this central aperture could have a circular form and the sets could be arranged with polygonic symmetry around this circular aperture.

Figure 2:
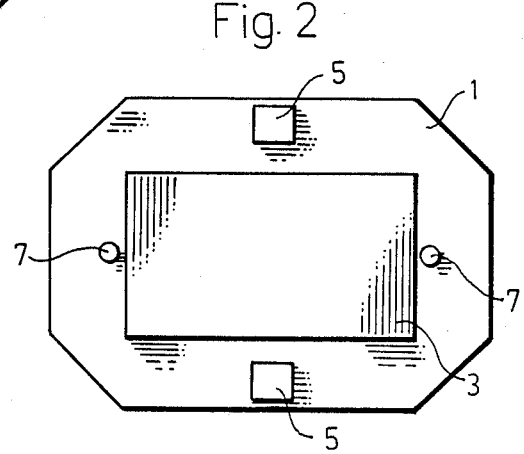
Figure 3:
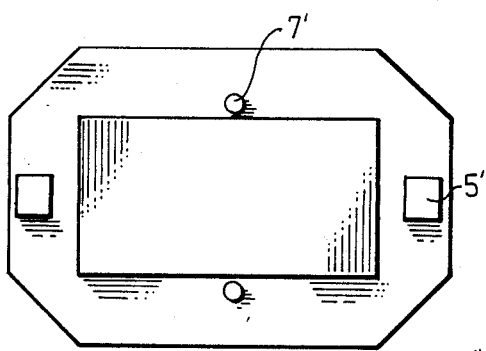
Figure 4:
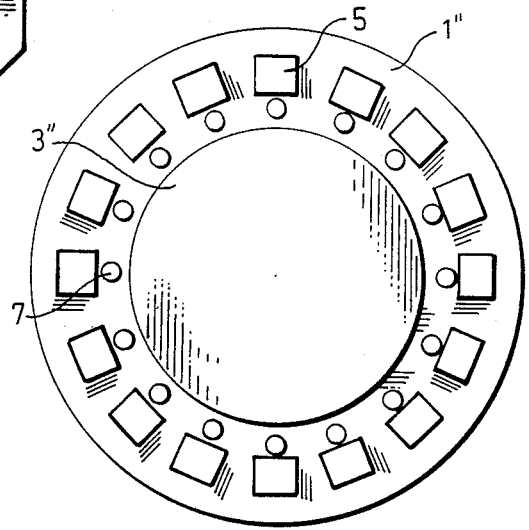

The invention will now be described with reference to the accompanying drawings in which FIG. 1 is a schematical view of a device for measuring the eye movements in two independent directions, FIG. 2 is a view of a device for measuring the eye movements in a vertical direction, FIG. 3 is a view of a device for measuring the eye movements in a horizontal direction and FIG. 4 is a view of a device provided with multiple sets of light detecting and emitting elements, intended for a precise measurement of eye movements in a selected direction.

In FIG. 2 a device according to the invention is illustrated intended for measuring the eye movements in the vertical or y direction. The device is shown from the side of the device facing the eye, whose movements are to be determined. On a frame 1, provided with a centrally located aperture 3, in this case of a generally rectangular shape, there are arranged two light detecting elements 5 and two light emitting elements 7. These light detecting elements are arranged symmetrically with respect to the eye in a vertical plane or y-plane passing through the symmetry point of the eye. Next, the light emitting elements are arranged on a horizontal axis or x-axis of the same kind. These light emitting elements 7 are also arranged symmetrically with respect to the eye.

In operation the light emitting elements 7 provide pulses of light or other similar radiation, preferably IR-light, which is detected by the light detecting elements 5. For this the light emitting elements 7 and the light detecting elements are connected to suitable electronic circuits, a part of which could be found on the supporting frame 1. This frame could be a printed circuit board, provided with all necessary connecting lines. These will also be connected to some connecting elements for connection with remotely placed electronic driving and supervising circuits.

In FIG. 3 a similar set of cooperating light emitting elements 7' and light detecting elements 5' for measuring the movements of the eye in a horizontal direction is illustrated. In this case the light detecting elements 5' are located in a horizontal plane and the light emitting elements 7' are located in a vertical plane.

In FIG. 1 is shown how the sets of light emitting elements and light detecting elements of FIG. 2 and 3 could be combined into a device intended for measurement of the eye movements both in a horizontal and a vertical direction, that is along both the x- and y-axis. This device is obtained by superimposing the sets of light emitting and detecting elements of FIG. 2 and 3 upon each other and on the common frame 1. When the connected supervising electronic unit stimulates the eye to move in a vertical direction, that is the y-direction, only the set of light emitting elements according to FIG. 2 is activated. When the eye is stimulated to move in a horizontal direction, i.e. the x-direction, the set of light-emitting elements corresponding to the set depicted in FIG. 3 is activated. When the eye moves in directions which are not near either of these directions both sets will be activated alternatively, but in these cases e.g. a pulse delivered by the light emitting elements 7 will be issued first and detected by the light detecting elements 5 and after that a pulse will be emitted from the light emitting elements 7' and detected by the light detecting elements 5'. In this case the seperation of the eye movement into the two components of the movement along the horizontal and vertical axes will be achieved.

To enhance the sensitivity along any axis of possible eye movements multiple sets of cooperating light emitting and detecting elements according to FIG. 4 could be used. Here several sets of light emitting and detecting elements are arranged around the central aperture along distributed axes. Generally these different sets are arranged sYmmetrically with the same angular distance between two adjacent sets with respect to the symmetry point of the device. This also means, if the central aperture 3" has a circular shape, that this arrangement has a polygonic symmetry.

As mentioned above, in this embodiment the set of operating light emitting detecting elements best suited for measuring the actual eye movement is selected by means of the supervising electronic circuits and the signals given by this set are those most representative of the eye movement. Of course, the other sets could also be used for giving some supplementary or higher order information on the eye movement.

We claim:

1. A device for measuring the movements of an eye, comprising:
   a supporting frame having an aperture;
   a first pair of light emitting elements arranged on opposite sides of said supporting frame and located in a first plane;
   a first pair of light detecting elements arranged on opposite sides of said supporting frame and located in a second plane which is orthogonal to said first plane; and
   wherein said first pair of light emitting elements and said first pair of light detecting elements are arranged symmetrically about said eye and cooperate in detecting movement of said eye.

2. A device according to claim 1, wherein:
   said first pair of light detecting elements are arranged in parallel to a direction of movement of said eye.

3. A device according to claim 1, further comprising:
   a second pair of light emitting elements arranged on opposite sides of said supporting frame and located in said second plane;
   a second pair of light detecting elements arranged on opposite sides of said supporting frame and located in said first plane; and
   wherein said second pair of light emitting elements and said second pair of light detecting elements are arranged symmetrically about said eye.

4. A device according to claim 3, wherein:
   said second pair of light emitting elements are arranged in parallel to a second direction of movement of said eye.

5. A device according to claim 4, further comprising:
   a plurality of light emitting elements arranged in pairs so that each pair of said plurality of light emitting elements is arranged on opposite sides of said supporting frame and is located in a distinct plane;
   a plurality of light detecting elements arranged in pairs so that each pair of said plurality of light detecting elements is arranged on opposite sides of said supporting frame and is located in another distinct plane which is orthogonal to said distinct plane in which said each pair of said plurality of light emitting elements is located; and
   wherein said plurality of light detecting elements, said plurality of light emitting elements, said first pair of light emitting elements, said first pair of light emitting elements, said second pair of light emitting elements, and said second pair of light emitting elements are arranged symmetrically about said eye.

6. A device according to claim 5, wherein:
   said plurality of light detecting elements are for detecting any movement of said eye in a plurality of directions.

7. A device according to claim 6, wherein only one pair of light emitting elements of a set consisting of said first pair of light emitting elements, said second pair of light emitting elements and said plurality of light emitting elements is activated at a time.

8. A device according to claim 7, wherein:
   the pairs of light emitting elements in said set are alternately activated in a repetitive sequence when a measurement of said eye's movements along more than one axis is desired.

* * * * *